(12) United States Patent
Ishii et al.

(10) Patent No.: US 9,040,745 B2
(45) Date of Patent: May 26, 2015

(54) PROCESS FOR PRODUCING FLUOROSULFURIC ACID AROMATIC-RING ESTERS

(75) Inventors: Akihiro Ishii, Kawagoe (JP); Takehisa Ishimaru, Kawagoe (JP); Takako Yamazaki, Kawagoe (JP); Manabu Yasumoto, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/128,362

(22) PCT Filed: Jun. 15, 2012

(86) PCT No.: PCT/JP2012/065311
§ 371 (c)(1),
(2), (4) Date: Dec. 20, 2013

(87) PCT Pub. No.: WO2013/002040
PCT Pub. Date: Jan. 3, 2013

(65) Prior Publication Data
US 2014/0114088 A1    Apr. 24, 2014

(30) Foreign Application Priority Data
Jun. 29, 2011    (JP) .................................. 2011-143647

(51) Int. Cl.
*C07C 303/24*    (2006.01)

(52) U.S. Cl.
CPC .................................... *C07C 303/24* (2013.01)

(58) Field of Classification Search
CPC combination set(s) only.
See application file for complete search history.

(56) References Cited

U.S. PATENT DOCUMENTS

| 3,733,304 A * | 5/1973 | Firth et al. ..................... 528/175 |
| 2011/0201825 A1 | 8/2011 | Ishii et al. |
| 2011/0213176 A1* | 9/2011 | Ishii et al. ..................... 560/265 |

FOREIGN PATENT DOCUMENTS

| WO | 93/14107 | * | 7/1993 |
| WO | WO 2010/047266 A1 | | 4/2010 |

OTHER PUBLICATIONS

McGuire et al., J. Org. Chem., 1994, 59, 6683-6686.*
McGuire et al., "A Novel, Practical Synthesis of Estra-1,3,5(10)-triene-3,17 β-dicarboxylic Acid 17- *tert*-Butylamide (SK&F 105656) from Estrone, via a Palladium-Catalyzed Methoxycarbonylation of a 3-Fluorosulfonate," Journal of Organic Chemistry, 1994, pp. 6683-6686, vol. 59, American Chemical Society.
Lange et al., "Uber Aryl-fluorsulfonate, Ar. O . $SO_2F_2$," Ber. Dtsch. Chem. Ges. B, 1930, p. 2653, vol. 63, Germany (with abstract).
Cramer et al., "New Syntheses of Aryl Fluorides and Aryl Fluorosulfonates from Oxyfluorides of Sulfur," Journal of Organic Chemistry, 1961, pp. 4164-4165, vol. 26.
Roth et al., "Palladium Cross-Coupling Reactions of Aryl Fluorosulfonates: An Alternative to Triflate Chemistry," Journal of Organic Chemistry, 1991, pp. 3493-3496, vol. 56.
Greene et al., "Protective Groups in Organic Synthesis," 1999, 28 pages, John Wiley & Sons, Third Edition.
Tuji et al., "Organic Synthesis Developed Using Transition Metal; Its Various Reaction Modes & New Developments," 51 pages, 1997 (with abstract).
Charalambous et al., "Certain Factors Relating to the Formation of Alkyl and Aryl Sulphates and Chlorosulphates," Journal of Chemical Society, 1964, pp. 5480-5482.
Hedayatullah et al., "Synthesis of hindered aryl fluorosulfates," Chemical Abstracts, 1980, p. 688 and cover page, vol. 93, No. 15.
International Search Report dated Sep. 4, 2012 with English translation (five (5) pages).
Japanese-language Written Opinion (PCT/ISA/237) dated Sep. 4, 2012 (four (4) pages).
"Preparation of Aromatic Polysulfates and Copoly (Sulfate Carbonates)," Journal of Polymer Science, Polymer Letters Edition, 1972, pp. 637-641, vol. 10, No. 8.
English translation of document C10 (Written Opinion (PCT/ISA/237)), previously submitted on Dec. 20, 2013 (five (5) pages).

* cited by examiner

*Primary Examiner* — Karl J Puttlitz

(57) ABSTRACT

A production process of a fluorosulfuric acid aromatic-ring ester according to the present invention includes reaction of an aromatic-ring hydroxyl compound with sulfuryl fluoride ($SO_2F_2$) in the presence of a tertiary amine except pyridine and methylpyridine. The sulfuryl fluoride, used as the reactant in the production process according to the present invention, is widely adapted as a fumigant and is easily available on a large scale. Further, the target compound can be obtained rapidly with a high yield under moderate reaction conditions in the production process according to the present invention. In this way, all of the prior art problems can be solved in the production process according to the present invention. The production process according to the present invention is thus particularly useful for industrial production of the fluorosulfuric acid aromatic-ring ester.

6 Claims, No Drawings

PROCESS FOR PRODUCING FLUOROSULFURIC ACID AROMATIC-RING ESTERS

FIELD OF THE INVENTION

The present invention relates to a process for industrial production of fluorosulfuric acid aromatic-ring esters.

BACKGROUND ART

Fluorosulfuric acid aromatic-ring esters are useful as low-cost substitutes for trifluoromethanesulfonic acid aromatic-ring esters (Non-Patent Document 1). As typical production processes of fluorosulfuric acid aromatic-ring esters, there are known a process for producing a fluorosulfuric acid aromatic-ring ester by thermal decomposition of an arenediazonium fluorosulfate (Non-Patent Document 2), a process for producing a fluorosulfuric acid aromatic-ring ester with the use of sulfonylchloridefluoride ($SO_2ClF$) (Non-Patent Document 3) and a process for producing a fluorosulfuric acid aromatic-ring ester with the use of fluorosulfuric acid anhydride (Non-Patent Document 4). There is also known, as a technique relevant to the present invention, a process for producing a fluorosulfuric acid aromatic-ring ester with the use of sulfuryl fluoride ($SO_2F_2$) (Patent Document 1).

PRIOR ART DOCUMENTS

Patent Documents

Patent Document 1: U.S. Pat. No. 3,733,304

Non-Patent Documents

Non-Patent Document 1; J. Org. Chem. (U.S.), 1994, vol. 59, p. 6683
Non-Patent Document 2: Ber. Dtsch. Chem. Ges. B (Germany), 1930, vol. 63. p. 2653
Non-Patent Document 3: J. Org. Chem. (U.S.), 1961, vol. 26, p. 4164
Non-Patent Document 4: J. Org. Chem. (U.S.), 1991, vol. 56, p. 3493

SUMMARY OF THE INVENTION

Problems to be Solved by the Invention

In the processes of Non-Patent Document 2 and 4, however, the raw substrate material or reactant (i.e. arenediazonium fluorosulfate or fluorosulfuric acid anhydride) is difficult to obtain on a large scale. In the process of Non-Patent Document 3, the target compound cannot always be obtained with a high yield (the yield of the target compound ranges from 45 to 85%). In the process of Patent Document 1, the reaction conditions of high temperature and high pressure (120° C., 350 psi) or long reaction time (18 hours) are required for the reaction of the raw substrate material with sulfuryl fluoride in the presence of pyridine.

Under these circumstances, there has been a strong demand to develop an industrial production process for producing a fluorosulfuric acid aromatic-ring ester rapidly with a high yield under moderate reaction conditions by the use of a raw substrate material and a reactant both of which are easily available on a large scale.

It is an object of the present invention to produce an industrial production process of a fluorosulfuric acid aromatic-ring ester in which the above-mentioned problems have been solved.

Means for Solving the Problem

As a result of extensive researches, the present inventors have found that it is possible to produce a fluorosulfuric acid aromatic-ring ester by reacting an aromatic-ring hydroxyl compound with sulfuryl fluoride in the presence of a tertiary amine except pyridine and methylpyridine. The present invention is based on such a finding. In the present invention, the reaction can be completed when the reaction temperature is 75° C. or lower, when the pressure is 1.0 MPa or lower or when the reaction time is 12 hours or less. It is preferable to adopt either one of these reaction conditions, and is particularly preferable to combine any of these reaction conditions, for industrial production of the fluorosulfuric acid aromatic-ring ester.

Namely, the present invention includes a process for producing a fluorosulfuric acid aromatic-ring ester as set forth in the following inventive aspects 1 to 4.

[Inventive Aspect 1]
A process for producing a fluorosulfuric acid aromatic-rag ester of the general formula [2], comprising reaction of an aromatic-ring hydroxyl compound of the general formula [1] with sulfuryl fluoride ($SO_2F_2$) in the presence of a tertiary amine except pyridine and methylpyridine

   [1]

where Ar represents an aromatic-ring group or a substituted aromatic-ring group

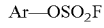   [2]

where A has the same meaning as in the general formula [1],
[Inventive Aspect 2]
The process according to Inventive Aspect 1, wherein the reaction is conducted at a reaction temperature of 75° C. or lower.
[Inventive Aspect 3]
The process according to Inventive Aspect 1 or 2, wherein the reaction is conducted at a reaction pressure of 1.0 MPa or lower.
[Inventive Aspect 4]
The process according to any one of Inventive Aspects 1 to 3, wherein the reaction is conducted in a reaction time of 12 hours or less.

The sulfuryl fluoride used in the production process according to the present invention is widely adapted as a fumigant and is easily available on a large scale. Further, the target compound can be obtained rapidly with a high yield under moderate reaction conditions in the production process according to the present invention. In Patent Document 1, not only pyridine but also triethylamine and methylpyridine are recited as a tertiary amine. However, the tertiary amine actually used in Examples of Patent Document 1 was only pyridine. The effects of the present invention (the rapid, high-yield production of the target compound under the moderate reaction conditions) are achieved only by the use of the tertiary amine except pyridine and methylpyridine (see Comparative Examples 1 to 3) and are not at all disclosed in Patent Document 1. In particular, there is no need to utilize high-pressure gas production equipment as the reaction can be conducted at a pressure of 1.0 MPa or lower. Furthermore, the crude product can be obtained with a high purity and thereby subjected to the subsequent reaction step such as coupling reaction without purification operation e.g. fractional distillation, recrystallization etc.

As mentioned above, all of the prior art problems can be solved in the production process according to the present invention. The production process according to the present invention is thus particularly useful for production of the fluorosulfuric acid aromatic-ring ester.

DETAILED DESCRIPTION OF EMBODIMENTS

Hereinafter, the production method of the fluorosulfuric acid aromatic-ring ester according to the present invention will be described below in detail. It is understood that: the scope of the present invention is not limited to the following embodiments; and various modifications and variations can be made to the following embodiments without departing from the scope of the present invention. All of the publications cited in the present specification, such as prior art documents and patent documents e.g. published patents and patent applications, are herein incorporated by reference.

In the production process according to the present invention, a fluorosulfuric acid aromatic-ring ester of the general formula [2] is produced by reaction of an aromatic-ring hydroxyl compound of the general formula [1] with sulfuryl fluoride ($SO_2F_2$) in the presence of a tertiary amine except pyridine and methylpyridine.

In the aromatic-ring hydroxyl compound of the general formula [1], Ar represents an aromatic-ring group or substituted aromatic-ring group. The aromatic-ring group is of 1 to 18 carbon atoms. Examples of the aromatic-ring group are: aromatic hydrocarbon groups, such as phenyl, naphthyl and anthryl; and aromatic heterocyclic groups each containing a heteroatom e.g. nitrogen, oxygen, sulfur etc., such as pyrrolyl (including nitrogen-protected form), pyridyl, furyl, thienyl, indolyl (including nitrogen-protected form), quinolyl, benzofuryl and benzothienyl.

Examples of the substituted aromatic-ring group are those obtained by substitution of any number of and any combination of substituents onto any of carbon or nitrogen atoms of the above aromatic-ring groups. As such substituents, there can be used: halogen atoms such as fluorine, chlorine, bromine and iodine; lower alkyl groups such as methyl, ethyl and propyl; lower unsaturated groups such as vinyl, allyl and propargyl; lower haloalkyl groups such as fluoromethyl, chloromethyl and bromomethyl; $C(CF_3)_2OH$ (including hydroxyl-protected form); lower alkoxy groups such as methoxy, ethoxy and propoxy; lower haloalkoxy groups such as fluoromethoxy, chloromethoxy and bromomethoxy; formyloxy group; lower acyloxy groups such as acetyloxy, propionyloxy and butylyloxy; cyano group; lower alkoxycarbonyl groups such as methoxycarbonyl, ethoxycarbonyl and propoxycarbonyl; lower alkoxycarbonyl lower alkyl groups such as methoxycarbonylmethyl, ethoxycarbonylethyl and propoxycarbonylpropyl; aromatic-ring groups such as phenyl, naphthyl, anthryl, pyrrolyl (including nitrogen-protected form), pyridyl, furyl, thienyl, indolyl (including nitrogen-protected form), quinolyl, benzofuryl and benzothienyl; protected carboxyl groups; protected amino groups; hydroxyl group; protected hydroxyl groups; and groups of the formula: X—Ar'—OH.

In the formula: X—Ar'—OH, X represents a $C(CH_3)_2$ group, $C(CF_3)_2$ group, oxygen atom, nitrogen atom (including nitrogen protected form), sulfur atom, SO group or $SO_2$ group; and A' represents a phenylene group or substituted phenylene group. The position of the substituent on the phenylene group is either 2-position, 3-position or 4-position relative to hydroxyl group. As the substituent of the substituted phenylene group, there can be used the same ones as those of the above substituted aromatic-ring group.

The following are specific examples of the aromatic-ring group substituted with X—Ar'—OH (the substituted aromatic-ring group).

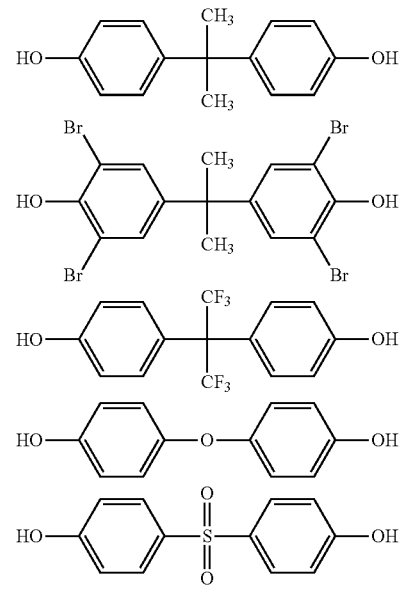

It is noted that, in the present specification, the term "lower" means that the group to which the term is attached is a group of 1 to 6 carbon atoms having a straight-chain structure, a branched structure or a cyclic structure (in the case of 3 or more carbons). The aromatic-ring group as the substituent of the aromatic-ring group may further be substituted with any of halogen atoms, lower alkyl groups, lower unsaturated groups, lower haloalkyl groups, $C(CF_3)_2OH$ (including hydroxyl-protected form), lower alkoxy groups, lower haloalkoxy groups, formyloxy group, lower acyloxy groups, cyano group, lower alkoxycarbonyl groups, lower alkoxycarbonyl lower alkyl group, protected carboxyl groups, protected amino groups, hydroxyl group; protected hydroxyl groups and groups of the formula: X—Ar'—OH. Examples of the protecting groups for the pyrrolyl, indolyl, hydroxyl, carboxyl and amino groups are those described in "Protective Groups in Organic Synthesis", Third Edition, 1999, John Wiley & Sons, Inc. Among others, it is preferable to use the aromatic-ring group or the aromatic-ring group substituted with any substituent other than "hydroxyl group", "aromatic-ring group" and "X—Ar'—OH group". Particularly preferred are the aromatic hydrocarbon group or the aromatic hydrocarbon group substituted with any substituent other than "hydroxyl group", "aromatic-ring group" and "X—Ar'—OH group" (substituted aromatic hydrocarbon group). In the case of an aromatic hydroxyl group having a plurality of hydroxyl groups, a plurality of fluorosulfonylation reactions may proceed depending on the reaction conditions adopted.

In the fluorosulfuric acid aromatic-ring ester of the general formula [2], Ar has the same meaning as in the aromatic-ring hydroxyl compound of the general formula [1].

Examples of the tertiary amine (except pyridine and methylpyridine) are triethylamine, diisopropylethylamine, tri-n-propylamine, tri-n-butylamine, N-methylpiperidine, 1-ethylpiperidine, N,N-dicyclohexylmethylamine, N,N- dicyclohexylethylamine, 4-dimethylaminopyridine, 1,5-diazabicyclo[4.3.0]nona-5-ene and 1,8-diazabicyclo[5.4.0]undec-7-ene. It is less preferable to use a strong basic tertiary amine such as 1,8-diazabicyclo[5.4.0]undec-7-ene because the use of such a strong basic tertiary amine causes generation of a considerable amount of diarylsulfate as a by-product (see Example 3). For this reason, triethylamine, diisopropylethylamine, tri-n-propylamine, tri-n-butylamine, N-methylpiperidine, 1-ethylpiperidine, N,N-dicyclohexylmethylamine and N,N-dicyclohexylethylamine are preferred. Particularly preferred are triethylamine, diisopropylethylamine, tri-n-propylamine, tri-n-butylamine, N-methylpiperidine and 1-ethylpiperidine. These bases can be used solely or in any combination thereof. In the present specification, the term "methylpyridine" refers to 2,6-lutidine, 2,4,6-collidine etc. (naturally including all of methyl positional isomers).

It suffices to use the tertiary amine (except pyridine and methylpyridine) in an amount of 0.7 mol or more per 1 mol of the aromatic-ring hydroxyl compound of the general formula [1]. The amount of the tertiary amine (except pyridine and methylpyridine) used is preferably 0.8 to 20 mol, more preferably 0.9 to 10 mol, per 1 mol of the aromatic-ring hydroxyl compound of the general formula [1].

It suffices to use the sulfuryl fluoride ($SO_2F_2$) in an amount of 0.7 mol or more per 1 mol of the aromatic-ring hydroxyl compound of the general formula [1]. The amount of the sulfuryl fluoride used is preferably 0.8 to 10 mol, more preferably 0.9 to 5 mol, per 1 mol of the aromatic-ring hydroxyl compound of the general formula [1].

The reaction can be conducted in a reaction solvent. Examples of the reaction solvent are: aliphatic hydrocarbon solvents such as n-hexane and n-heptane; aromatic hydrocarbon solvents such as toluene and xylene; halogenated solvents such as methylene chloride and 1,2-dichloroethane; ether solvents such as tetrahydrofuran, tert-butyl methyl ether and 1,2-dimethoxyethane; ester solvents such as ethyl acetate and n-butyl acetate; amide solvents such as N,N-methylformamide, 1-methyl-2-pyrrolidinone, N,N-dimethylacetoamide and 1,3-dimethyl-2-imidazolydinone; acetonitrile; dimethyl sulfoxide; and water. Among others, n-heptane, toluene, methylene chloride, tetrahydrofuran, 1,2-dimethoxyethane, ethyl acetate, N,N-dimethylformamide, 1,3-dimethyl-2-imidazolidinone, acetonitrile, dimethyl sulfoxide and water are preferred. Particularly preferred are toluene, methylene chloride, tetrahydrofurane, 1,2-dimethoxy ethane, ethyl acetate, N,N-dimethylformamide and acetonitrile. These reaction solvents can be used solely or in any combination thereof.

It suffices to use the reaction solvent in an amount of 0.01 L (liter) or more per 1 mol of the aromatic-ring hydroxyl compound of the general formula [1]. The amount of the reaction solvent used is preferably 0.05 to 20 L, more preferably 0.1 to 10 L, per 1 mol of the aromatic-ring hydroxyl compound of the general formula [1]. Alternatively, the reaction can be conducted in a neat condition without the use of the reaction solvent (see Example 6).

Further, it suffices that the reaction temperature is in the range of −80 to +100° C. The reaction temperature is preferably in the range of −60 to +75° C., more preferably −40 to +50° C.

It suffices that the reaction pressure is in the range of 2.0 MPa to atmospheric pressure. The reaction pressure is preferably 1.0 to 0.001 MPa, more preferably 0.8 to 0.002 MPa.

It suffices that the reaction temperature is 24 hours or less. The reaction time is preferably 12 hours or less, more preferably 6 hours or less. As the reaction time varies depending on the raw substrate material, reactant and reaction conditions, it is preferable to determine the time at which there can be seen almost no decrease of the raw substrate material as the end of the reaction while monitoring the progress of the reaction by any analytical means such as gas chromatography, liquid chromatography or nuclear magnetic resonance.

The fluorosulfuric acid aromatic-ring ester of the general formula [2] can be obtained by any ordinary post treatment operation for organic synthesis. The resulting crude product can be purified to a high purity, as needed, by activated carbon treatment, fractional distillation, recrystallization, column chromatography or the like.

The thus-obtained fluorosulfuric acid aromatic-ring ester can be used as an electrophilic reagent for various coupling reactions by transition metal catalysts. Typical examples of the coupling reaction are name reactions such as Kumada-Tamao-Corriu coupling reaction, Migita-Kosugi-Stille coupling reaction, Suzuki-Miyaura coupling reaction, Negishi coupling reaction and Hiyama coupling reaction.

It is feasible to use the fluorosulfuric acid aromatic-ring ester for any reaction other than the coupling reaction. For example, the fluorosulfuric acid aromatic-ring ester can be used as a substitute for pseudohalide reaction as discussed in "Organic Synthesis Developed Using Transition Metal; Its Various Reaction Modes & New Developments" (Jiro TUJI et al., Kagaku Dojin, 1997). The fluorosulfuric acid aromatic-ring ester can also suitably be used for alkoxycarbonylation reaction (see Non-Patent Document 1 (J. Org. Chem. (U.S.), 1994, vol. 59, p. 6683) etc.)

In the production process according to the present invention, the reaction completed solution contains a stoichiometric amount of fluoride (salt or complex of the tertiary amine except pyridine and methylpyridine and hydrogen fluoride) as a by-product. The desired reaction of the subsequent step may sometimes be promoted due to the existence of such a fluoride. In this case, it is feasible to intentionally omit the post treatment and continuously subject the reaction completed solution to the subsequent reaction as one-pot reaction for favorable reaction results. In the case where the reaction completed solution is separated into two phases, it is feasible to recover the phase containing the fluorosulfuric acid aromatic-ring ester and directly subject the recovered phase to the subsequent desired reaction.

EXAMPLE

The present invention will be described in more detail below with reference to the following examples. It should be understood that the following examples are illustrative and are not intended to limit the present invention thereto.

Example 1

Into a 50-mL pressure-proof reaction vessel of stainless steel (SUS), 5.00 g (30.8 mmol, 1.00 eq) of an aromatic-ring hydroxyl compound of the following formula, 15.0 mL (0.5 L/mol) of toluene and 4.70 g (46.4 mmol, 1.51 eq) of triethylamine were charged.

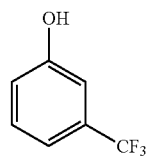 [SMILES: Oc1cccc(C(F)(F)F)c1]

Then, 4.70 g (46.1 mmol, 1.50 eq) of sulfuryl fluoride was gradually blown from a cylinder into the reaction vessel. The resulting solution was stirred for 2 hours at room temperature. The pressure inside the reaction vessel was 1.0 MPa or lower throughout the material charging and reaction steps. It was confirmed by gas chromatography analysis of the reaction completed solution that the conversion rate of the reaction was 100%.

The reaction completed solution was diluted with 30 mL of toluene, washed with 15 mL of water, washed with 10 mL of 1N hydrochloric acid, washed with 10 mL of saturated aqueous sodium hydrogencarbonate solution, and then, further washed with 10 mL of saturated sodium chloride solution. The recovered organic phase was concentrated under a reduced pressure and dried under a vacuum.

There was thus obtained 5.68 g of a fluorosulfuric acid aromatic-ring ester of the following formula.

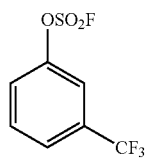

The yield of the target compound was 76%. The gas chromatographic purity of the target compound was 97.0% (the content of the toluene as the reaction solvent was 2.7%) The $^1$H-NMR and $^{19}$F-NMR measurement results of the target compound were indicated below.

$^1$H-NMR (standard material: Me$_4$Si, deuterated solvent: CDCl$_3$] δ ppm: 7.57 (Ar—H, 1H), 7.63 (Ar—H, 1H), 7.66 (Ar—H, 1H), 7.72 (Ar—H, 1H).

$^{19}$F-NMR (standard material: C$_6$F$_6$, deuterated solvent: CDCl$_3$] δ ppm: 98.86 (s, 3F), 200.12 (s, 1F).

Example 2

Into a 50-mL pressure-proof reaction vessel of stainless steel (SUS), 4.05 g (25.0 mmol, 1.00 eq) of an aromatic-ring hydroxyl compound of the following formula. 25.0 mL (1 L/mol) of toluene and 6.95 g (37.5 mmol, 1.50 eq) of tri-n-butylamine were charged.

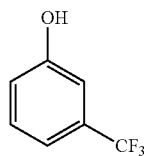

Then, 3.83 g (37.5 mmol, 1.50 eq) of sulfuryl fluoride was gradually blown from a cylinder into the reaction vessel. The resulting solution was stirred for 3 hours at room temperature. The pressure inside the reaction vessel was 1.0 MPa or lower throughout the material charging and reaction steps. It was confirmed by gas chromatography analysis of the reaction completed solution that the conversion rate of the reaction was 81%.

The reaction completed solution was diluted with 50 mL of toluene, washed with 50 mL of 1N hydrochloric acid, washed twice with 40 mL of 5% aqueous sodium hydrogencarbonate solution, and then, further washed with 40 mL of saturated sodium chloride solution. It was confirmed by $^{19}$F-NMR measurement of the recovered organic phase that there existed a fluorosulfuric acid aromatic-ring ester of the following formula.

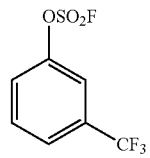

The $^{19}$F-NMR measurement results of the target compound were the same as those of Example 1.

Example 3

Into a 50-mL pressure-proof reaction vessel of stainless steel (SUS), 4.05 g (25.0 mmol, 1.00 eq) of an aromatic-ring hydroxyl compound of the following formula, 25.0 mL (1 L/mol) of toluene and 5.71 g (37.5 mmol, 1.50 eq) of 1,8-diazabicyclo[5.4.0]undec-7-ene were charged.

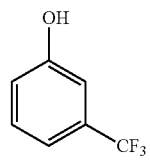

Then, 3.83 g (37.5 mmol, 1.50 eq) of sulfuryl fluoride was gradually blown from a cylinder into the reaction vessel. The resulting solution was stirred for 3 hours at room temperature. The pressure inside the reaction vessel was 1.0 MPa or lower throughout the material charging and reaction steps. It was confirmed by gas chromatography analysis of the reaction completed solution that the conversion rate of the reaction was 100%.

The reaction completed solution was diluted with 50 mL of toluene, washed with 50 mL of 1N hydrochloric acid, washed with 50 mL of 5% aqueous sodium hydrogencarbonate solution, and then, further washed with 20 mL of 10% sodium chloride solution. The recovered organic phase was concentrated under a reduced pressure and dried under a vacuum. There was thus obtained a fluorosulfuric acid aromatic-ring ester of the following formula,

The $^{19}$F-NMR measurement results of the target compound were the same as those of Example 1. It was further confirmed by $^{19}$F-NMR measurement (internal standard material: α,α,α-trifluorotoluene) that the target compound was contained in an amount of 1.83 g. The yield of the target compound was 30%. The gas chromatographic purity of the target compound was 30.3%. There was contained 67.3% of a diaryl sulfate of the following formula.

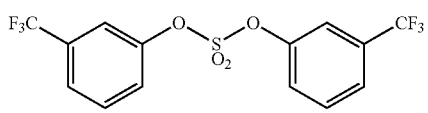 [SMILES: O=S(=O)(Oc1cccc(C(F)(F)F)c1)Oc1cccc(C(F)(F)F)c1]

Example 4

Into a 50-mL pressure-proof reaction vessel of stainless steel (SUS), 3.80 g (25.0 mmol, 1.00 eq) of an aromatic-ring hydroxyl compound of the following formula, 25.0 mL (1 L/mol) of toluene and 4.91 g (38.0 mmol, 1.52 eq) of diisopropylethylamine were charged.

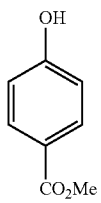

Then, 4.10 g (40.2 mmol, 1.61 eq) of sulfuryl fluoride was gradually blown from a cylinder into the reaction vessel. The resulting solution was stirred for 4 hours at room temperature. The pressure inside the reaction vessel was 1.0 MPa or lower throughout the material charging and reaction steps. It was confirmed by gas chromatography analysis of the reaction completed solution that the conversion rate of the reaction was 100%.

There was thus obtained a fluorosulfuric acid aromatic-ring ester of the following formula.

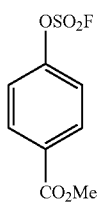

The selectivity of the target compound was 96.3%. The $^1$H-NMR and $^{19}$F-NMR measurement results of the target compound were indicated below.

$^1$H-NMR (standard material: Me$_4$Si, deuterated solvent: CDCl$_3$] δ ppm: 7.43 (Ar—H, 2H), 8.17 (Ar—H, 2H).

$^{19}$F-NMR (standard material: C$_6$F$_6$, deuterated solvent: CDCl$_3$] δ ppm: 200.43 (s, 1F).

Example 5

Into a 300-mL pressure-proof reaction vessel of stainless steel (SUS), 15.2 g (99.9 mmol, 1.00 eq) of an aromatic-ring hydroxyl compound of the following formula, 100 mL (1 L/mol) of toluene and 15.2 g (150 mmol, 1.50 eq) of triethylamine were charged.

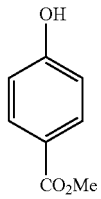

Then, 15.3 g (150 mmol, 1.50 eq) of sulfuryl fluoride was gradually blown from a cylinder into the reaction vessel. The resulting solution was stirred for 3 hours at room temperature. The pressure inside the reaction vessel was 1.0 MPa or lower throughout the material charging and reaction steps. It was confirmed by gas chromatography analysis of the reaction completed solution that the conversion rate of the reaction was 100%.

The reaction completed solution was diluted with 100 mL of toluene, washed with 50 mL of 1N hydrochloric acid, washed with 50 mL of saturated aqueous sodium hydrogencarbonate solution, and then, further washed twice with 20 ml, of saturated sodium chloride solution. The recovered organic phase was dried with anhydrous sodium sulfate, concentrated under a reduced pressure and dried under a vacuum.

There was thus obtained 23.1 g of a fluorosulfuric acid aromatic-ring ester of the following formula.

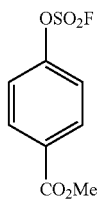

The yield of the target compound was 99%. The gas chromatographic purity of the target compound was 99.7%. The $^{19}$F-NMR measurement results of the target compound were the same as those of Example 4.

Example 6

Into a 50-mL pressure-proof reaction vessel of stainless steel (SUS), 10.8 g (99.9 mmol, 1.00 eq) of an aromatic-ring hydroxyl compound of the following formula and 12.1 g (120 mmol, 1.20 eq) of triethylamine were charged.

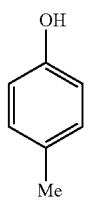

Then, 12.2 g (120 mmol, 1.20 eq) of sulfuryl fluoride was gradually blown from a cylinder into the reaction vessel. The resulting solution was stirred for 3 hours and 30 minutes at room temperature. The pressure inside the reaction vessel was 1.0 MPa or lower throughout the material charging and reaction steps. It was confirmed by gas chromatography analysis of the reaction completed solution that the conversion rate of the reaction was 100%.

The reaction completed solution was diluted with 60 mL of ethyl acetate and washed with 40 mL of water. The recovered aqueous phase was extracted with 20 mL of ethyl acetate. The recovered organic phases were combined together. The combined organic phase was washed with 15 mL of 1N hydrochloric acid, 15 mL of saturated aqueous sodium hydrogencarbonate solution, and then, further washed with 15 mL of saturated sodium chloride solution. The washed organic phase was dried with anhydrous sodium sulfate, concentrated under a reduced pressure and dried under a vacuum.

There was thus obtained 16.9 g of a fluorosulfuric acid aromatic-ring ester of the following formula.

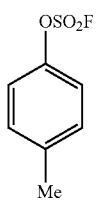

The yield of the target compound was 89%. The gas chromatographic purity of the target compound was 99.6% (the content of the 4-methylphenol as the raw substrate material was 0.2%) The $^1$H-NMR and $^{19}$F-NMR measurement results of the target compound were indicated below.

$^1$H-NMR (standard material: Me$_4$Si, deuterated solvent: CDCl$_3$] δ ppm: 2.39 (s, 3H), 7.21 (Ar—H, 2H), 7.26 (Ar—H, 2H).

$^{19}$F-NMR (standard material: C$_6$F$_6$, deuterated solvent: CDCl$_3$] δ ppm: 198.78 (s, 1F).

Example 7

Into a 50-mL pressure-proof reaction vessel of stainless steel (SUS), 830 mg (4.99 mmol, 1.00 eq) of an aromatic-ring hydroxyl compound of the following formula, 15.0 mL (3 L/mol) of 1,2-dimethoxyethane and 1.15 g (11.4 mmol, 2.28 eq) of triethylamine were charged.

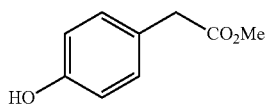

Then, 510 mg (5.00 mmol, 1.00 eq) of sulfuryl fluoride was gradually blown from a cylinder into the reaction vessel. The resulting solution was stirred for 10 hours at room temperature. The pressure inside the reaction vessel was 1.0 MPa or lower throughout the material charging and reaction steps.

It was confirmed by $^1$H-NMR measurement of the reaction completed solution that the conversion rate of the reaction was 100%. It was further confirmed by $^1$H-NMR and $^{19}$F-NMR measurements of the reaction completed solution that there existed a fluorosulfuric acid aromatic-ring ester of the following formula as a main product.

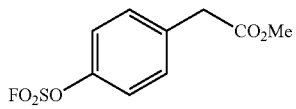

The $^1$H-NMR and $^{19}$F-NMR measurement results of the target compound were indicated below.

$^1$H-NMR (standard material: Me$_4$Si, deuterated solvent: CDCl$_3$] δ ppm: 3.67 (s, 2H), 3.72 (s, 3H), 7.31 (Ar—H, 2H), 7.40 (Ar—H, 2H).

$^{19}$F-NMR (standard material: C$_6$F$_6$, deuterated solvent: CDCl$_3$] δ ppm: 199.23 (s, 1F).

Comparative Example 1

Into a 50-mL pressure-proof reaction vessel of stainless steel (SUS), 4.05 g (25.0 mmol, 1.00 eq) of an aromatic-ring hydroxyl compound of the following formula, 25.0 mL (1 L/mol) of toluene and 2.97 g (37.5 mmol, 1.50 eq) of pyridine were charged.

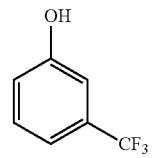

Then, 3.83 g (37.5 mmol, 1.50 eq) of sulfuryl fluoride was gradually blown from a cylinder into the reaction vessel. The resulting solution was stirred for 2 hours and 30 minutes at room temperature.

It was confirmed by gas chromatography analysis of the reaction completed solution that the conversion rate of the reaction was 0%. It was further confirmed by $^{19}$F-NMR measurement of the reaction completed solution that there did not exist a fluorosulfuric acid aromatic-ring ester of the following formula.

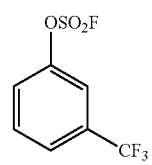

As a result, the desired reaction did not proceed with the use of pyridine. It is assumed that the severe reaction conditions as disclosed in Patent Document 1 (U.S. Pat. No. 3,733,304) are required in order for the desired reaction to proceed with the use of pyridine.

Comparative Example 2

Into a 50-mL pressure-proof reaction vessel of stainless steel (SUS), 4.05 g (25.0 mmol, 1.00 eq) of an aromatic-ring hydroxyl compound of the following formula, 25.0 mL (1 L/mol) of toluene and 4.02 g (37.5 mmol, 1.50 eq) of 2,6-lutidine were charged.

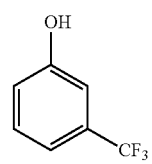

Then, 3.83 g (37.5 mmol, 1.50 eq) of sulfuryl fluoride was gradually blown from a cylinder into the reaction vessel. The resulting solution was stirred for 2 hours and 30 minutes at room temperature.

It was confirmed by gas chromatography analysis of the reaction completed solution that the conversion rate of the reaction was 0%. It was further confirmed by $^{19}$F-NMR measurement of the reaction completed solution that there did not exist a fluorosulfuric acid aromatic-ring ester of the following formula.

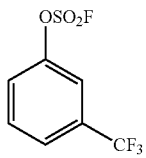

As a result, the desired reaction did not proceed with the use of 2,6-lutidine. It is also assumed that the severe reaction conditions as disclosed in Patent Document 1 (mentioned above) are required in order for the desired reaction to proceed with the use of 2,6-lutidine.

Comparative Example 3

Into a 50-mL pressure-proof reaction vessel of stainless steel (SUS), 3.80 g (25.0 mmol, 1.00 eq) of an aromatic-ring hydroxyl compound of the following formula, 25.0 mL (1 L/mol) of toluene and 3.26 g (41.2 mmol, 1.65 eq) of pyridine were charged.

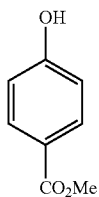

Then, 4.20 g (41.2 mmol, 1.65 eq) of sulfuryl fluoride was gradually blown from a cylinder into the reaction vessel. The resulting solution was stirred for 4 hours at room temperature.

It was confirmed by gas chromatography analysis of the reaction completed solution that the conversion rate of the reaction was 0%. It was further confirmed by $^{19}$F-NMR measurement of the reaction completed solution that there did not exist a fluorosulfuric acid aromatic-ring ester of the following formula.

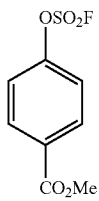

Although the same reaction was conducted by changing the amount of the pyridine to 1.53 eq and changing the amount of the sulfuryl fluoride to 1.49 eq, the conversion rate of the reaction was 0%. The reaction results were reproducible.

As a result, the desired reaction did not proceed with the use of pyridine. It is also assumed that the severe reaction conditions as disclosed in Patent Document 1 (mentioned above) are required in order for the desired reaction to proceed with the use of pyridine.

As described above, the production process according to the present invention enables rapid, high-yield production of the target fluorosulfuric acid aromatic-ring ester under moderate reaction conditions with the use of the raw substrate material and reactant that are easily available on a large scale.

INDUSTRIAL APPLICABILITY

The target compound of the present invention, that is, fluorosulfuric acid aromatic-ring ester is suitable for use as intermediates for pharmaceutical and agrichemical products.

The invention claimed is:
1. A process for producing a fluorosulfuric acid aromatic-ring ester of the general formula [2], comprising reaction of an aromatic-ring hydroxyl compound of the general formula [1] with sulfuryl fluoride ($SO_2F_2$) in the presence of a tertiary amine

Ar—OH        [1]

where Ar represents a phenyl naphthyl or anthryl group that may or may not have any number of and any combination of substituents selected from the group consisting of halogen atoms, lower alkyl groups, lower unsaturated groups, lower haloalkyl groups, $C(CF_3)_2OH$ group, lower alkoxy groups, lower haloalkoxy groups, lower acyloxy groups, cyano group, lower alkoxycarbonyl groups, lower alkyloxycarbonyl lower alkyl groups, protected carboxyl groups, protected amino groups and protected hydroxyl groups;

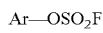

Ar—$OSO_2F$        [2]

where Ar has the same meaning as in the general formula [1],
wherein the reaction is conducted at a reaction temperature of −40 to +50° C. and at a reaction pressure of 1.0 MPa or lower; and
wherein the tertiary amine is at least one selected from the group consisting of triethylamine, diisopropylethylamine, tri-n-propylamine, tri-n-butylamine, N-methylpiperidine, 1-ethylpiperidine, N,N-dicyclohexylmethylamine and N,N-dicyclohexylethylamine.

2. The process according to claim 1, wherein the reaction is conducted in a reaction time of 12 hours or less.

3. The process according to claim 1, wherein the reaction is conducted in a neat condition without the use of a reaction solvent.

4. A process for producing a fluorosulfuric acid aromatic-ring ester of the general formula [2], comprising reaction of an aromatic-ring hydroxyl compound of the general formula [1] with sulfuryl fluoride ($SO_2F_2$) in the presence of a tertiary amine

Ar—OH        [1]

where Ar represents a phenyl group having any number of and any combination of substituents selected from the group consisting of $CH_3$, $CF_3$, $CO_2CH_3$ and $CH_2CO_2CH_3$;

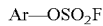

Ar—$OSO_2F$        [2]

where Ar has the same meaning as in the general formula [1],
wherein the reaction is conducted at a reaction temperature of −40 to +50° C. and at a reaction pressure of 1.0 MPa or lower; and wherein the tertiary amine is at least one selected from the group consisting of triethylamine, diisopropylethylamine and tri-n-butylamine.

5. The process according to claim 4, wherein the reaction is conducted in a reaction time of 12 hours or less.

6. The process according to claim 4, wherein the reaction is conducted in a neat condition without the use of a reaction solvent.

* * * * *